United States Patent [19]

Fritsch et al.

[11] Patent Number: 5,438,142
[45] Date of Patent: Aug. 1, 1995

[54] FUNCTIONALIZED TRIS (HYDROXYPHENYL) COMPOUNDS

[75] Inventors: John R. Fritsch; Olan S. Fruchey; Debasish Kuila; George Kvakovszky; Mark A. Murphy; Michael T. Sheehan; James R Sounik; Richard Vicari, all of Corpus Christi, Tex.

[73] Assignee: Hoechst Celanese Corp., Somerville, N.J.

[21] Appl. No.: 105,824

[22] Filed: Aug. 10, 1993

Related U.S. Application Data

[63] Continuation-in-part of Ser. No. 921,450, Jul. 28, 1992, abandoned, which is a continuation-in-part of Ser. No. 829,123, Feb. 3, 1992, abandoned.

[51] Int. Cl.⁶ ............... C07D 249/16; C07D 249/20; C08F 26/06; C08K 5/34
[52] U.S. Cl. .................. 546/240; 548/260; 548/257; 548/258; 548/259; 548/261; 562/74; 568/337; 568/720
[58] Field of Search ............ 548/260, 257, 259, 258, 548/261; 546/240; 562/74; 568/337, 720

[56] References Cited

U.S. PATENT DOCUMENTS

| | | | |
|---|---|---|---|
| 4,812,575 | 3/1989 | Vogl et al. | 548/260 |
| 4,835,284 | 5/1989 | Seino | 548/260 |
| 4,845,180 | 7/1989 | Henry et al. | 548/260 |
| 4,943,637 | 7/1990 | Seino et al. | 548/260 |
| 5,099,027 | 3/1992 | Vogl et al. | 548/259 |

FOREIGN PATENT DOCUMENTS 0031302  7/1981  European Pat. Off. ............ 548/260

OTHER PUBLICATIONS

Functional Polymers. XVI. Synthesis and Polymerization of 2(2–Hydroxy–5–Isopropenyphenyl)–2H–Benzotriazole and a New Synthesis of 2(2–Hydroxy–5–Vinylphenyl)2H–Benzotriazole of Nir, Vogl and Gupta, Journal of Polymer Science (1982).

Functional Polymers XLV. Incorporation of Dihydroxy 2(2–Hydroxyphenyl)2H–Benzotriazole Dericatives Into Polyesters of Gomez and Vogl, Polymer Journal, vol. 18, No. 5, pp. 429–437 (1986).

*Primary Examiner*—Floyd D. Higel
*Attorney, Agent, or Firm*—Michael W. Ferrell

[57] ABSTRACT

Compounds useful as polymer stabilizers which are polymerizable into condensation polymer systems are disclosed and claimed. A particularly preferred embodiment is 1-(3'-(benzotriazol-2"-yl)-4'-hydroxyphenyl)-1,1-bis(4-hydroxyphenyl)ethane.

2 Claims, 2 Drawing Sheets

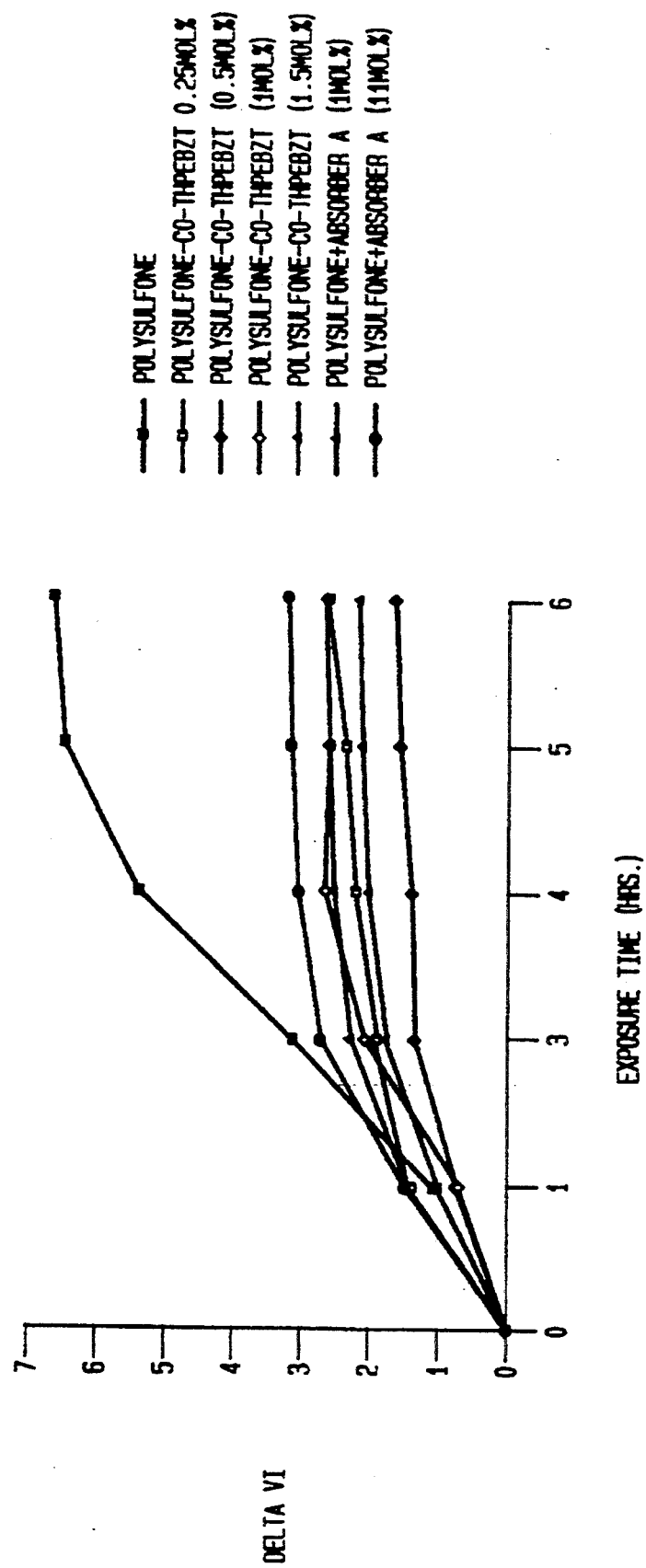

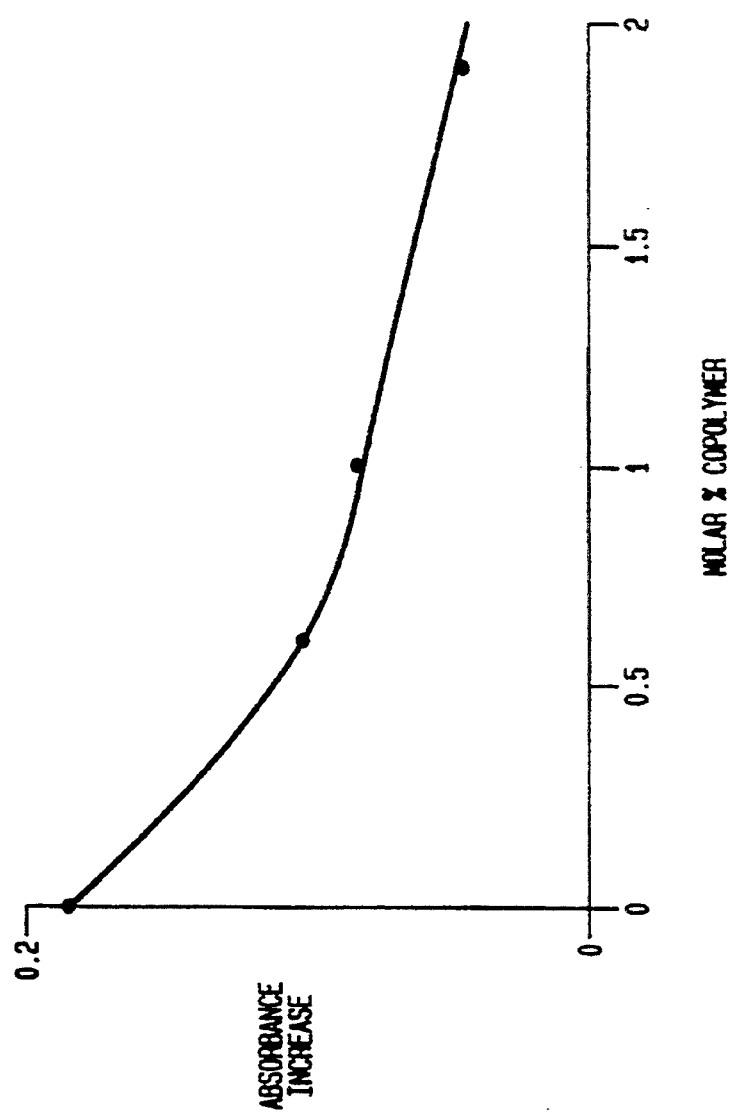

FUNCTIONALIZED TRIS (HYDROXYPHENYL) COMPOUNDS

CROSS REFERENCE TO RELATED APPLICATIONS

This application is a continuation in part of U.S. patent application Ser. No. 921,450, filed Jul. 28, 1992 now abandoned which was a continuation in part of U.S. patent application Ser. No., 829,123 filed Feb. 3, 1992, also abandoned. Related applications include the following:

U. S. Ser. No. 07/478,072, filed Feb. 9, 1990, entitled, PURIFICATION OF 1,1,1-TRIS (4'-HYDROXYPHENYL)ETHANE (THPE) now U.S. Pat. No. 4,992,598;

U.S. Ser. No. 07/576,630, filed Aug. 31, 1990, entitled, ACRYLATE ESTERS OF 1,1,1-TRISHYDROXYPHENYLETHANE (THPE) now abandoned;

U. S. Ser. No. 07/595,887, filed Oct. 11, 1990, entitled, ACRYLATE ESTERS OF 1,1,1 -TRISHYDROXYPHENYLETHANE (THPE) now U.S. Pat. No. 5,130,467;

U. S. Ser. No. 07/989,397, filed Dec. 11, 1992, entitled, PROCESS FOR PREPARING 1-TRIS (4'-HYDROXYPHENYL)ETHANE now abandoned;

U.S. Ser. No. 07/819,167, filed Jan. 8, 1992, entitled, PROCESS FOR THE PREPARATION OF 1,3,5TRIS(4'-HYDROXYPHENYL)BENZENE & ITS DERIVATIVES & INTERMEDIATE COMPOUNDS, now abadoned;

U.S. Ser. No. 07/819,168, filed Jan. 8, 1992, entitled, PROCESS FOR THE PREPARATION OF 1,3,5-TRIS(4'-HYDROXYARYL)BENZENE now abandoned;

U.S. Ser. No. 08/068,460, filed May 27, 1993, entitled PROCESS FOR THE PREPARATION OF 1,3,5-TRIS(4'-HYDROXYARYL)BENZENE now U.S. Pat. No. 5,300,698;

U.S. Ser. No. 07/819,166, filed Jan. 8, 1992, entitled, EPOXIDATION PRODUCTS OF 1,3,5-TRIS(4'-HYDROXYPHENYL)BENZENES now abandoned;

U.S. Pat. No. 08/069,966, filed May 28, 1993, entitled AMINES DERIVED FROM THPE & PROCESSES FOR PREPARING THE SAME now U.S. Pat. No 5,312,988; and U.S. Ser. No. 08/069,966, filed May 28, 1993, entitled, POLYAMINES DERIVED FROM THPB & PROCESSES FOR PREPARING THE SAME now U.S. Pat. No. 5,300,559.

TECHNICAL FIELD

The present invention relates to novel compounds which include a triaryl or quadaryl nucleus coupled to a stabilizing or colorant moiety. The novel compounds, relatively high in molecular weight, are particularly suitable for incorporation into condensation polymers.

BACKGROUND OF INVENTION

Additives to impart ultraviolet ("UV") stabilizing properties or antioxidant properties to polymers or to perform as colorants are known. For example, the Uvinul TM materials (BASF Corporation, Chemicals Division, Parsippany, N.J.) and the Tinuvin TM additives (Ciba-Geigy Corporation, Additives Department, Hawthorne, N.Y.) are ultraviolet stabilizers that are commercially available for use with polymers. Such additives generally are low molecular weight species, and have several problems including poor compatibility with the polymer matrix, poor dispersion into the polymer formulation, migration within the polymer, losses due to volatility of the additive material during processing or use, and leaching into liquids, for instance, when fabrics made of stabilized polymeric fibers are washed.

One method of overcoming this problem is to incorporate stabilizers directly into the polymer; for example, nitroso compounds are directly incorporated into synthetic rubbers, while amine and phenol antioxidants have been grafted onto synthetic elastomers to form masterbatch concentrates which are subsequently blended with pure polymer. Nir and Vogl have disclosed 2-(2-hydroxy-5-vinylphenyl)-2H-benzotriazole and polymers thereof as ultraviolet stabilizers in addition polymer systems. Nir, Z., and Vogl, O., Journal of Polymer Science; Polymer Chemistry Edition Vol. 20, pp. 2735–2754 Wiley and Sons, (1982). Similar subject matter is described in U.S. Pat. Nos. 5,099,027; 4,943,637 and 4,812,575. See also Gomez, P. M. and Vogl, O. Polymer Journal, Volume 18, No. 5 pp. 429–437 (1986) which discloses dihydroxy benzotriazole compounds.

SUMMARY OF INVENTION

The present invention is directed in a first aspect to substituted multi-aryl compounds useful for incorporation into condensation polymers. The substitutions forming a part of the subject matter of the invention include those useful as antioxidants, colorants, ultraviolet (UV) light stabilizers, flame retardants and stain blockers such as hindered amines, diazoarenes, benzotriazoles, aroyls including benzophenones, branched alkyl groups, halides, phosphates, phosphites, phosphonites, and sulfonates. The foregoing substitutents are attached to a triaryl or quadaryl nucleus having bifunctionality suitable for incorporation into condensation polymers.

More specifically, there is included within the present invention functionalized compounds capable of being incorporated into a condensation polymer having a triaryl or quadaryl nucleus and including at least a first structural unit selected from group I and chemically bonded thereto at least a second substituent structural unit selected from group II wherein group I is:

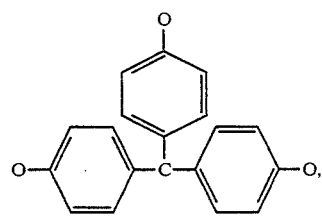

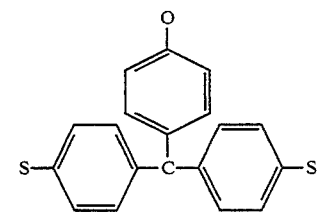

-continued

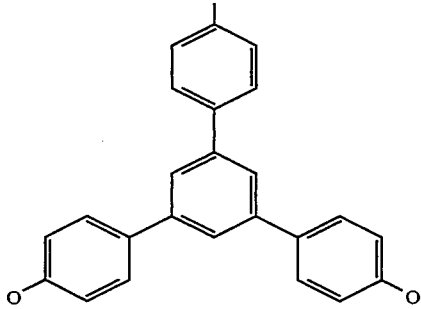

and group II is hindered amines; diazoarenes; aroyls including benzophenones; benzotriazoles; branched alkyl groups; a halide selected from the group consisting of chlorine, bromine or iodine; phosphates; phosphites; phosphonates and phosphonites; and sulfonates. Preferably, group I is

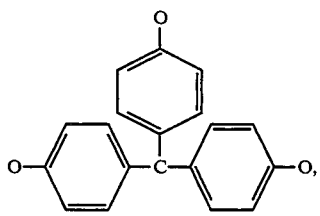

or

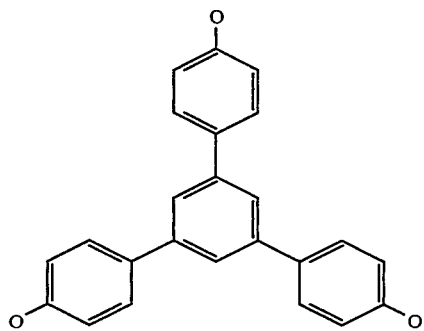

and group II is

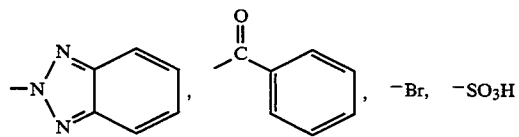

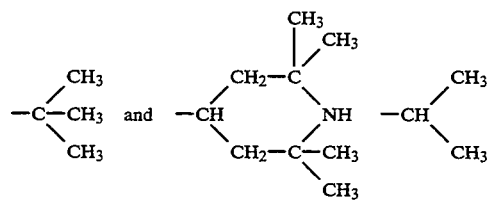

where the extending line indicates a bond site to the group I nucleus.

A particularly preferred compound for UV stabilization is 1-(3'-(benzotriazol-2''-yl)-4'-hydroxyphenyl)-1,1-bis(4-hydroxyphenyl)ethane ("THPE-BZT"); while the following compounds are useful as antioxidants, color-ants, flame retardants, stain blockers and for UV stabilization:

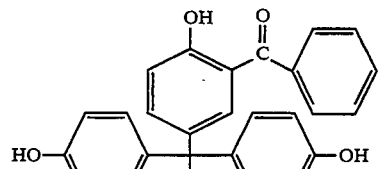

(UV Stabilizer)

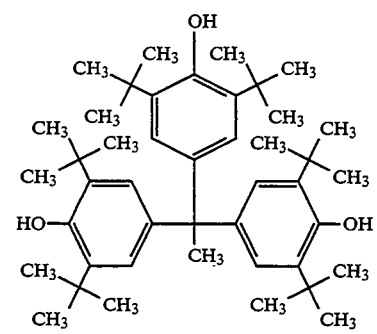

(Anti Oxidant)

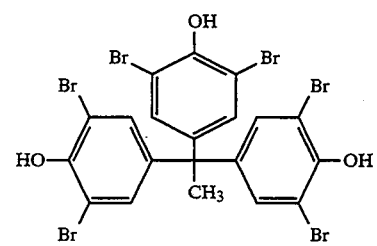

(Flame Retardant)

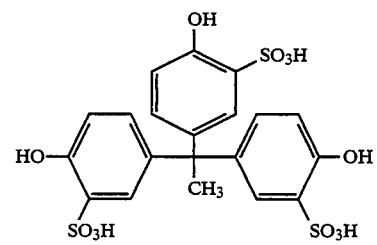

(Stain Blocker)

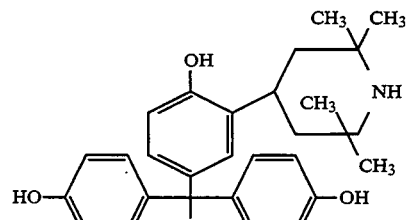

(UV Stablilizer)

In another aspect of the invention, the foregoing compounds are incorporated into condensation polymers such as polyesters, polycarbonates, polyurethanes, polysulfones and epoxy resins.

In a further aspect of the invention, there is disclosed and claimed a method of preparing 3-(benzotriazol-2'- yl)-4-hydroxyacetophenone (4-HAP-BZT) comprising preparing 3-(2'-nitrophenylazo)-4hydroxyacetophenone (4-HAP-AZO) and reductively cyclizing the 4-HAP-AZO.

In still further aspects of the invention, preferred methods of preparing and purifying diazoarene derivatives of 4-hydroxyacetophenone are disclosed and claimed and it was discovered that water increases solubility of the inventive compounds in certain organic solvents.

BRIEF DESCRIPTION OF DRAWINGS

The invention is described in detail below in connection with numerous examples and various figures in which:

FIG. 1 is a plot showing the relative stability to ultraviolet light of certain polysulfone polymers prepared in accordance with the present invention; and FIG. 2 is a plot showing the relative stability to ultraviolet light of certain polycarbonate polymers prepared in accordance with the present invention.

DETAILED DESCRIPTION

The invention is described in detail below for purposes of illustration only and not by way of limitation. One of skill in the art will readily appreciate that ingredients may be substituted and reaction conditions altered from the specific examples hereinafter provided.

One may practice the present invention by synthesizing (THPE-BZT) as shown in SCHEME 1 below.

present invention. By employing condensation polymerization, polymers such as polysulfones, polyesters, polycarbonates, polyurethanes, polyethers, epoxies, and the like may be produced. Suitable hydroxy comonomers for condensation polymerization include 1,4-dihydroxybenzene, 1,3-dihydroxybenzene, 2,6-dihydroxynaphthalene, 1,5-dihydroxynaphthalene, 4,4'-dihydroxybiphenyl, 2,2-di(4'-hydroxyphenyl)propane (bisphenol A), 2,2-di(4'-hydroxyphenyl)-1,1,1,3,3,3-hexafluoropropane (hexafluorobisphenol A), 1,1-di(4'-hydroxyphenyl)ethane, di(4'-hydroxyphenyl)methane, and the like. Other comonomers such as, for example, ethylene glycol, 1,2-propylene glycol, 1,3-propanediol, neopentylglycol, 1,4-butanediol, and the like, may also be used.

Suitable carboxyl and like comonomers for condensation polymerization include phosgene, dimethyl carbonate, diethyl carbonate, diphenyl carbonate, thionyl chloride, sulfuryl chloride, dimethyl sulfate, diethyl sulfate, terephthalic acid, terephthaloyl dichloride, dimethyl terephthalate, diethyl terephthalate, isophthalic acid, isophthaloyl dichloride, dimethyl isophthalate, diethyl isophthalate, 4,4'-biphenyldicarboxylic acid, 4,4'-biphenyldicarboxylic acid dichloride, dimethyl 4,4'-biphenyldicarboxylate, diethyl 4,4'-biphenyldicarboxylate, 1,3-benzenedisulfonyl dichloride, dimethyl 1,3-benzenedisulfonate, diethyl 1,3-benzenedisulfonate, 4,4'-biphenyldisulfonyl dichloride, dimethyl 4,4-biphenyldisulfonate, diethyl 4,4'-biphenyldisulfonate, 6,2-naphthalenedicarboxylic acid, 6,2-naph-

SCHEME 1

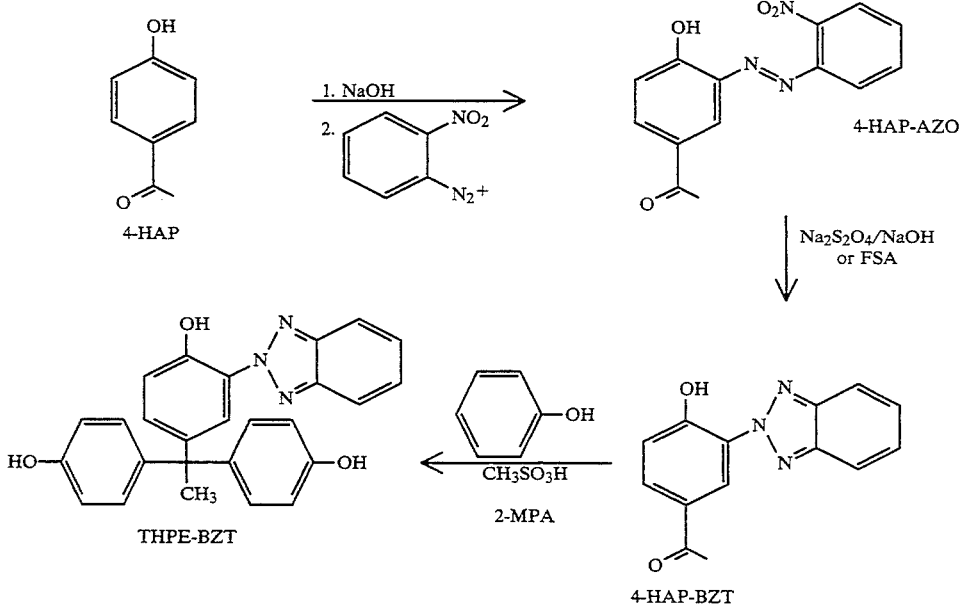

The general procedure of SCHEME 1 may be used to produce a variety of substituted compounds with multiple ring systems by way of suitable reactants such as diazoarenes useful as colorants for polymers, hindered amines useful as antioxidants or phosphates, phosphites, phosphonates, or phosphonites useful as flame retardants as well as the aroyls, benzotriazoles branched alkyl groups and sulfonates specifically exemplified hereinafter.

Suitable compounds of the present invention may be homopolymerized or copolymerized via condensation polymerization to produce further embodiments of the thalenedicarboxylic acid dichloride, dimethyl 6,2-naphthalenedicarboxylate, diethyl 6,2-naphthalenedicarboxylate, 1,5-naphthalenedicarboxylic acid, 1,5-naphthalenedicarboxylic acid dichloride, dimethyl 1,5-naphthalenedicarboxylate, diethyl 1,5-naphthalenedicarboxylate, 1,5-naphthalenedisulfonic acid dichloride, dimethyl 1,5-naphthalenedisulfonate, diethyl 1,5-naphthalenedisulfonate, 2,6-naphthalenedisulfonic acid dichloride, dimethyl, 2,6-naphthalenedisulfonate, diethyl 2,6-naphthalenedisulfonate, oxalic acid, oxalyl dichloride, dimethyl oxalate, diethyl oxalate, malonic acid, malonyl dichloride, dimethyl malonate, diethyl malonate, succinic acid, succinic anhydride, succinyl dichloride, dimethyl succinate, diethyl succinate, maleic acid, maleic anhydride, dimethyl maleate, diethyl maleate, and the like. Other monomers may include isocyanates, glycidyl ethers and epichlorohydrin.

The following Examples describe suitable processes to synthesize some representative compositions of the present invention. Thus, for example, while some of the Examples may illustrate the synthesis of 4-hydroxyacetophenone ("4-HAP") derivatives, it is to be understood that where appropriate, similar derivatives with the foregoing Formulas may also be prepared by following similar procedures.

EXAMPLE 1

4-HAP-AZO

A 1-L round bottom flask was charged with 400 g of ice water and 90 mL concentrated HCl. While stirring and cooling with an ice bath 69 g of o-nitroaniline was added. The slurry was cooled to 0° C. and a solution composed of 38 g sodium nitrite and 88 g water was added slowly over a 20 minute period. The flask contents were stirred at 0° C. for 1.5 hrs. The excess nitrite was quenched with urea and the solution placed in an addition funnel. The addition funnel was fitted to a 2-L round bottom flask which contained 650 mL water, 21 g sodium hydroxide, 68 g 4-HAP, and 38 g sodium carbonate. The diazonium salt solution was then added to the stirred flask over a 30 minute period while the temperature was held under 5° C. with an ice bath. The slurry was stirred for 40 minutes in the ice bath, then the bath removed and the contents warmed to room temperature and stirred for 1 hr. The solids were filtered and dried in a vacuum oven at 65° C. yielding 148 g of a red solid. LC analysis revealed the solid was 40.5% 4-HAP-azo, 16.9% Unknown 1, 4.1% Unknown 2, 1.45% 4-HAP, and 11.8% water.

EXAMPLE 2

4-HAP-AZO Alternate Procedure

A 1-L round bottom flask was charged with 375 g ice/water, 90 mL concentrated HCl and 68 g o-nitroaniline. The slurry was cooled to 0° C. and a solution composed of 35.9 g sodium nitrite and 88mL water was added over a 30 minute period. The flask contents were then stirred at 0° C. for 1.5 hrs. The excess nitrite was consumed with sulfamic acid and the solution placed in an addition funnel. A second addition funnel was charged with a solution composed of 550 g water, 20 g sodium hydroxide, and 68 g 4-HAP. The two addition funnels were attached to a 5-L flask which was charged with 1500 g of ice water and 40 mL pyridine. The contents of the flask were stirred and cooled with an ice bath while the contents of the two addition funnels were added simultaneously over a 30 minute period. A simultaneous addition period of as short as five or 10 minutes may be used. The contents of the flask were stirred at 0° C. for 4 hrs. and then filtered. The solids were dried in a vacuum oven at 65° C. yielding 106 g of red solids. LC analysis revealed 63.9% 4-HAP-AZO, 3.1% unknown 1, 2.3% unknown 2, 1.8% 4-HAP, and 0.3% water.

EXAMPLE 3

4-HAP-BZT

A 2-L round bottom flask was fitted with a mechanical stirrer, a thermowell, and a condenser. The flask was charged with 106 g of 4 HAP-AZO from above, 250 mL water, 500 mL isopropanol, and 182 g 50% sodium hydroxide. The solution was stirred under nitrogen then 72 g of formamidinesulfinic acid was added in one portion. The temperature rose to 79° C. and the contents were heated at reflux for 1 hr. The inorganic salts were filtered and the solution cooled to 35° C. with an ice bath, and 75 mL of concentrated HCl was added to adjust the solution to pH 4.5. The slurry was stirred for 2 hrs at room temperature, then filtered. The solids were washed with 200 mL of water and dried in a vacuum oven at 65° C. yielding 53.5 g of solids which were 94.1% 4-HAP-BZT and 1.7% others by LC.

Example 4

Reductive Cyclization of 3-(2'-nitrophenylazo)-4-hydroxyacetophenone (4-HAP-AZO) to 3-(benzotriazol-2'-yl)-4-hydroxyacetophenone (4-HAP-BZT)

A methanol solution of 5.50% by weight sodium hydroxide is prepared. 4-HAP-AZO is added to the amount of this methanol solution containing a molar quantity of sodium hydroxide equal to 14.9 times the moles of starting 4-HAP-AZO. A solution of water (52.7 wt %), methanol (41.7 wt %), sodium dithionite ($Na_2S_2O_4$, 4.26 wt %), and sodium hydroxide (1.28 wt %) is prepared. To the mixture of 4-HAP-AZO in methanolic sodium hydroxide stirred at 75° C. under nitrogen is added over 15 minutes the amount of the aqueous methanol solution containing a molar quantity of sodium dithionite equal to 2.00 times the moles of starting 4-HAP-AZO. The reaction mixture is then stirred at 75° C. under nitrogen for five hours prior to filtration. The filtrate is diluted with a volume of water equal to the volume of methanol in the sodium hydroxide solution to which the starting 4-HAP-AZO was added. On acidification with aqueous HCl to pH 5, the filtrate precipitates solid 4-HAP-BZT. The solid 4-HAP-BZT is recovered by filtration and washed with 0–5° C. water.

The procedure of this Example was used to produce 0.2081 moles of 4-HAP-BZT from 0.3648 moles of 4-HAP-AZO as a crude solid. The crude solid 4-HAP-BZT was purified by recrystallization from diethyl ether.

EXAMPLE 5

4-HAP-BZT

An alternate procedure to produce 4-HAP-BZT from 4-HAP-AZO is to catalytically hydrogenate 4-HAP-AZO. This procedure was used as follows:

The following ingredients were charged to a 100 cc pressure reactor fitted with a temperature controller, a hydrogen regulator and stirrer:

5.5 g 4-HAP-AZO
14.0 g Toluene
6.3 g Methanol
1.3 g Diethylamine
0.4 g 5% Pd/C

The reactor was purged twice with 50 Psi nitrogen by alternately pressuring up with nitrogen then slowly opening the vent followed by pressure checking the reactor for 20 minutes with 200 psi nitrogen. After a successful pressure check the reactor was vented and purged twice with 50 psi hydrogen. The hydrogen regulator was set at 50 psi, and the valve opened during the reaction while the stirrer was activated and the temperature maintained at 35° C. for 30 minutes. After 30 minutes, the temperature was increased to 50° C. and maintained for an additional hour. The heater was then turned off and the reactor allowed to cool to room temperature while the reactor was de-pressurized, purged and the 4-HAP-BZT product was removed and recovered in at least 40% yield.

EXAMPLE 6

4-HAP-BZT

A 5-L four neck round bottom flask was fitted with an overhead stirrer, an addition funnel, a thermowell, and a nitrogen purge. The flask was charged with 2100 g of ice water, 540 mL concentrated HCl, and 414 g o-nitroaniline. The contents were stirred and cooled with an ice bath for 30 minutes then a solution composed of 215 g sodium nitrite and 525 g water was added slowly over a 40 minute period while holding the temperature at 5° C. When the addition was complete the contents were allowed to stir at 5° C. for 2 hrs. The excess nitrite was then destroyed with sulfamic acid (5 g sulfamic acid dissolved in 50 mL water). Starch iodide paper was used to confirm absence of nitrite. A 12-L flask four neck flask was fitted with an overhead stirrer, an addition funnel, a thermowell and a nitrogen purge. The flask was charged with 3300 g ice water, 120 g sodium nydroxide pellets, 408 g 4-hydroxyacetophenone, 225 g sodium carbonate and 1000 g ice. The contents were stirred and cooled to 5° C. and then the diazonium salt solution added over a 40 minute period while holding the temperature under 10° C. The contents were allowed to stir at 10° C. for 2.5 hrs and then warm to room temperature and stand stirring overnight. The next morning the solids were filtered and slurried with 3 L of isopropanol and returned to the 12-L flask. The flask was fitted with a reflux condenser and a heating mantle and then 909 g of 50% sodium hydroxide added yielding a homogeneous soluton. Next, 389 g of formamidine sulfinic acid was added and the contents stirred for 1 hr during which time the exotherm caused the temperature to rise to 78° C. Then 480 g of 50% sodium hydroxide was added and 324 g of formamidine sulfinic acid added in three portions over a 15 minute period. The contents were allowed to reflux for 2 hrs and then stand overnight. The next day the inorganic solids were removed by filtration and the filtrate acidified to pH 3 with concentrated HCl. The slurry was stirred and cooled for 1 hr and the solids filtered and washed with 1 L of water. Drying in a vacuum oven overnight yielded 318 g of 4-HAP-BZT which assayed at 91.4% purity.

EXAMPLE 7

4-HAP-BZT to THPE-BZT

A four neck 12-L round bottom flask was equipped with an air cooled reflux condenser, an overhead stirrer, a thermowell, and an addition funnel. The flask was charged with 760 g of 4-HAP-BZT and 2400 g molten phenol. The contents were stirred and a nitrogen purge started. Then 321 g of 2-mercaptopropionic acid ("2-MPA") was charged through the addition funnel. The addition funnel was charged with 318 g of methanesulfonic acid. The methanesulfonic acid was added slowly over 30 minutes to hold the exotherm under 52° C. The flask was fitted with a temperature controlled heating mantle and the contents stirred at 52° C. for 21 hrs. The next day the heating mantle was removed and 2100 g of ice cold methanol was added to the flask and the contents cooled with an ice bath to 4° C. and stirred for 1 hr. The slurry was filtered through a coarse fitted filter and the solids washed with two 1050 g portions of cold methanol. The crude THPE-BZT solid was slurried and stirred for 10 minutes with a solution composed of 100 mL concentrated ammonium hydroxide and 1950 mL water. The slurry was filtered and washed with 2000 mL of water. The solids were placed in a 12-L round bottom flask which contained 560 mL water, 8 L acetone, and 25 g activated carbon. The contents were stirred and refluxed under nitrogen for 2 hrs. Then 50 g of Celite was added and the mixture stirred for 10 minutes. The slurry was filtered through a celite pad and allowed to cool to room temperature. A few drops of concentrated HCl was added to decrease the color of the filtrate. The filtrate was transferred to a carboy and 8 L of water was added slowly while stirring vigorously. The carboy was then placed in a cold box at 8° C. and allowed to stand overnight. The next day the slurry was filtered and the white solids washed with two 3 L portion of water. The purified solids were dried in a vacuum oven at 60° C. yielding 1011 g of white solids which assayed at 99% THPE-BZT.

Examples 8,9

Alternative Purification of Crude THPE-BZT

Crude THPE-BZT prepared as above was dissolved in either isopropanol or preferably, acetone. The resulting brownish solution was then eluted through an Amberlyst-21 basic ion exchange resin pretreated by elution with isopropanol followed by acetone. The sample was eluted with acetone. The resulting yellow solution was treated with 5% aq. HCl, until pH<7. Water was then added to the acetone solution until it became slightly turbid. A reddish-brown oil precipitated out and solidified upon standing at room temperature. Analysis of this material by LC showed it contained THPE-BZT, and two unknowns. The white turbid solution decanted from the colored oil was allowed to precipitate slowly to yield a white solid which was filtered, washed with water and dried on the filter. Analysis of this material by LC showed it contained THPE-BZT, and two unknowns. After slow precipitation of the white solid from the acetone solution the solid was filtered, washed with water and dried on the filter. Recovery was 80 to 87% depending on purity of the starting material and was increased to 92% by recycling the reddish-brown solid through the purification process. Purity of the resulting THPE-BZT was 99+%. In another run, Amberlyst-15, an acidic ion exchange resin, was substituted for the aqueous acid treatment. Here the crude THPE-BZT was treated with Amberlyst-21 followed by Amberlyst-15. Water was added to the yellow acetone solution until it turned slightly turbid. Again, a reddish-brown oil precipitated out first. The supernatant was decanted from the turbid solution. The second crop yielded (white) THPE-BZT recovered in 85% yield. Purity was 99+%. Runs made with isopropanol as the solvent did not result in a reddish-brown oil precipitating, and, as expected the APHA colors were higher and the overall purities were lower in these cases.

THPE-BZT in the anhydrous form is not generally soluble in aprotic organic solvents such as diethyl ether, $CH_3CN$, tetrahydrofuran and the like. In contrast, protic solvents like dimethyl sulfoxide and N,N dimethyl formamide will readily dissolve THPE-BZT in either hydrated or anhydrous form. If it is desired to dissolve anhydrous THPE-BZT in an aprotic organic solvent, the solvent may be mixed with from 1 to 50 weight percent water based on the solvent/water mixture, preferably from about 1 to 10 percent water to promote dissolution of the THPE-BZT. Alternatively, the hydrated form will readily dissolve in aprotic solvents.

EXAMPLE 10

Preparation of the tribenzoate of tris(4-hydroxyphenyl)ethane:

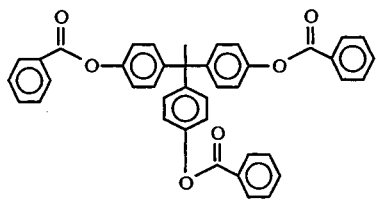

An aqueous NaOH solution (80 g in 200 g $H_2O$) containing tris(4-hydroxyphenyl)ethane (prepared in accordance with Example 7, except that only unsubstituted 4-HAP is used) (153 g, 0.5 mol) and a phase transfer catalyst, tetrabutyl ammonium bromide (1 g) was added dropwise to a rapidly stirred solution of benzoyl chloride (212 g, 1.5 mol) in 200 g $CH_2Cl_2$ at room temperature. After the addition was complete the two-phase mixture started to reflux. Refluxing ended in 20 minutes. The reaction was stirred for an additional two hours. Then the water layer was decanted and the organic layer washed with water, dried over $MgSO_4$ and rotovap to yield a white solid. The white solid was recrystallized from acetone to give 295.18 g (96% yield) of the tribenzoate, MP=224° C.

EXAMPLE 11

Conversion of the Tribenzoate to the Tribenzophenone

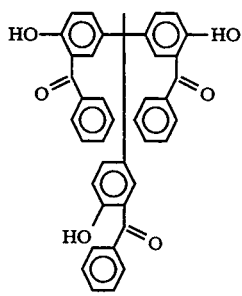

Tris(4-hydroxyphenyl)ethane tribenzoate (1.69 g, 2.7 mmol) was dissolved in degassed HPLC grade THF (100 g). The colorless solution was poured into an Ace-Hanovia photochemical reactor. The solution was photolyzed for 6 to 12 hours. The resulting bright yellow solution showed no starting benzoate by thin-layer chromatography (silica gel, 20% acetone/toluene). LC analysis showed a mixture containing the Fries rearranged products, mono (8%), di (31%) and tri (30%). The benzophenone structures were confirmed by IR, MS, and NMR. No starting material was detected.

EXAMPLE 12

Fries Rearrangement of Tris(4'-hydroxyphenyl)ethane Tribenzoate to the Tribenzophenone Tris(4'-hydroxyphenyl)ethane tribenzoate is added to a stirred autoclave. The reactor is evacuated then chilled to about −30° C. Anhydrous HF (about 12 times the weight of the starting tribenzoate ester) is now added via suction to about half-fill the reactor. The contents of the vessel are heated at about 55° C. for about 5 hours. The reactor contents are vented (via a dip tube) onto about 8 times their weight of wet ice and neutralized with potassium hydroxide to a pH of about 6.5. The crude solid tribenzophenone product is filtered on a Buchner funnel. Pure 1,1,-tris(3'-benzoyl-4'-hydroxyphenyl)ethane may be obtained by recrystallization from acetone, chloroform or other suitable solvent.

EXAMPLE 13

Production of 3'-Benzoyl-4'-hydroxyacetophenone by Ring Benzoylation of 4-HAP

Anhydrous $AlCl_3$ (3.09 moles) is weighed and transferred under nitrogen to flask fitted with a mechanical stirrer, a nitrogen inlet, and an exit bubbler. To the $AlCl_3$ is added 9.19 moles of 1,2-dichloroethane and 1.160 moles of benzotrichloride. The resulting mixture is stirred on an ice bath at 0° C. for 10 minutes before addition of 4-HAP (1.00 mole), in portions, at 0° C. with immediate evolution of HCl fumes. The reaction mixture is stirred at 0° C. for an additional 15 minutes before being poured over about 4.0 times its weight of ice-water. The resulting aqueous mixture is stirred and heated at 70° C. for 30 minutes and then extracted with about 4.57 moles of 1,2-dichloroethane. Vacuum rotary evaporation of the 1,2-dichloroethane extract provides crude 3'-benzoyl-4'-hydroxyacetophenone, which can be purified by distillation, recrystallization, or HPLC.

The procedure of this Example 13 was used to produce 3'-benzoyl-4'-hydroxyacetophenone (1.994 moles, 60.1% yield) from 4'-hydroxyacetophenone (3.32 moles) and benzotrichloride (3.85 moles); which may then be used to produce substituted THPE compounds.

EXAMPLE 14

Alkylation of tris(4-hydroxyphenyl)ethane with

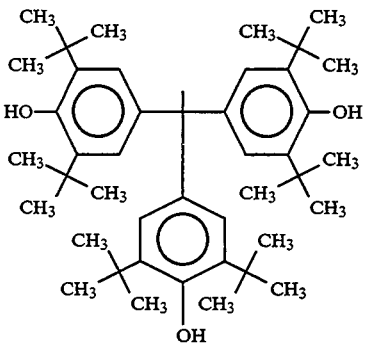

isobutylene

Tris(4-hydroxyphenyl)ethane 3 g, 9.8 mmol) is heated in 25 mL of tolune with 0.03 g of aluminum powder at 100° C. in an autoclave. At this point isobutylene (68.6 mmol) is added. The mixture is maintained at 100° C. to complete the reaction. The pressure in the autoclave is held at 100 psi. The reaction time is 7 hours. The resulting product is isolated by evaporation of the toluene. Similarly, the isopropyl analog is readily synthesized.

EXAMPLE 15

3,5-Di-t-butyl-4-hydroxyacetophenone

A mixture of 2,6-di-t-butylphenol (41.1 g, 0.20 moles) and glacial acetic acid (17.8 g, 0.30 moles) was slowly added to freshly distilled trifluoroacetic anhydride (60.8 g, 0.29 moles) over a period of 30 minutes. The temperature was maintained at 25° C. using a water bath. The mixture was stirred at room temperature for an additional 22 hours and then was diluted with methyl-t-butyl ether (175 mL). The solution was carefully neutralized with sodium bicarbonate (20% wt/wt) and the organic layer was washed with water (3×300 mL). The solution was reduced to a solid under vacuum and was recrystallized from MTBE, vacuum dried (r.t., 24 hours, 5 torr), and weighed (31.0 g, 0.13 mole, 62.6%). $^1$H NMR (CDCl$_3$) δ ppm 7.86 (s,Ar—H), 5.75 (s, OH), 2.56 (s,C=OCH$_3$), 1.19 (s,C(CH$_3$)$_3$).

EXAMPLE 16

1,1-Bishydroxyphenyl-1-(3',5'-di-t-butyl-4'-hydroxyphenyl)ethane

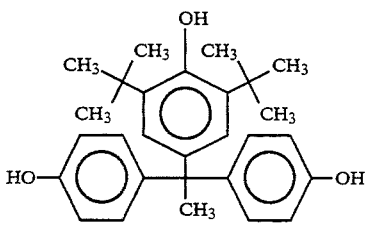

A mixture of 3,5-Di-t-butyl-4-hydroxyacetophenone (7.8 g, 0.031 moles) and phenol (25.89 g, 0.28 moles) was heated to 80° C. Mercaptoproprionic (3.8 g, 0.06 moles) and methanesulfonic acid (3.2 g, 0.03 moles) were slowly added over a period of 30 minutes. The mixture was maintained at 80° C. for 24 hours and then cooled to room temperature. Phenol was removed by distillation under vacuum (80° C., 1 torr) to give a dark red oil. The oil was diluted with methanol and maintained at 0° C. for 2 weeks. The methanol was removed under vacuum to give a red solid (11.4 g, 0.027 moles, 87.2%). $^{13}$C NMR (CDCl$_3$) δ ppm 49.9 (s, CH$_3$C—).

EXAMPLE 17

Preparation of Tris-1,1,1-(3,5'-dibromo-4'-hydroxyphenyl)ethane

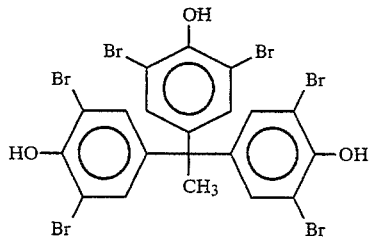

A 1 L three neck round bottom flask is equipped with a thermometer, an addition funnel and a reflux condenser which is connected to a gas scrubber. The flask is charged with 30.6 g (0.1 mol) trishydroxyphenylethane and 300 mL of glacial acetic acid. The contents of the flask are stirred and a 15° C. water bath is placed around the flask. The addition funnel is charged with 96 g (0.6 mol) bromine. The bromine is added dropwise to the stirred flask over a 2 hr period while holding the temperature at 15° C. The contents of the flask are stirred for an additional 2 hrs and then added to a beaker containing 1000 mL water. The solid which precipitates out is filtered and is washed with water. The solid is then dried in a vacuum oven.

EXAMPLE 18

Preparation of 1',1'',1'''-trishydroxy-1,1,1-triphenylethane-2',2'',2'''-trisulfonic acid or 1,1,1-tris(p-hydroxyphenyl)ethane-3',3'',3'''-trisulfonic acid

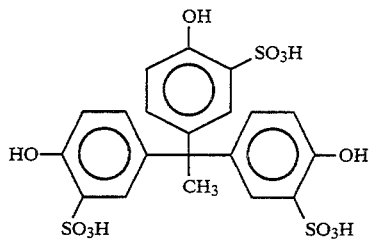

A 1-L round bottom flask is charged with 30.6 g trishydroxyphenylethane (0.1 mol) and 500 mL concentrated sulfuric acid. The flask is fitted with a reflux condenser. The flask is heated with a water bath at 60° C. for 4 hrs while being stirred. The contents of the flask are poured on to 2000 g of ice and the solid is filtered and washed with water. The solid is dried in a vacuum oven. This material is particularly useful as a stain-blocker when incorporated into a polymer as described hereinafter. Similarly, the trinitro analog of like utility is readily made.

EXAMPLES 19, 20

The following examples 19 and 20 relate to hindered amine light stabilizer (HALS) compounds of the present invention.

EXAMPLE 19

Production of HALS Derivative
1-[3'-2',2'',6'',6''-tetramethylpiperidine-4''-yl)-4'-hydroxyphenyl]-1,1-bis(4'''-hydroxyphenyl)ethane AlCl₃ (3 moles) is added slowly to a stirred mixture of 1,1,1-tris(4'-hydroxyphenyl)ethane(1 mole) and 4-chloro-2,2,6,6-tetramethylpiperidine (1.00 mole, *Helv. Chim. Acta* 49 (1966) at P. 694) in nitrobenzene (5 L) maintained at 25° C. with cooling as necessary. HCl gas, formed as a byproduct, is vented throughout the entire reaction period. The reaction mixture is stirred and heated to 65° C. for 45 minutes, cooled to 25° C., and then added slowly to three times its weight of water maintained at 5°–25° C. with cooling. The resulting aqueous mixture is extracted with diethyl ether. The aqueous phase of the extraction is neutralized to pH 8 by addition of 25 wt % aqueous NaOH with cooling to 25° C. The resulting aluminum salt precipitate is removed by filtration, and the aqueous filtrate is extracted with diethyl ether. All the diethyl ether extracts are combined and evaporated to a residue of non-volatile reaction products, from which the HALS product is isolated by recrystallization, distillation, or HPLC.

EXAMPLE 20

Production of HALS Derivative
1-[3'-(2'',2'',6'',6''-tetramethylpiperidine-4''-yl)-4'-hydroxyphenyl]-1,1-bis(4'''-hydroxyphenyl)ethane 2,2,6,6-Tetramethyl-1,2,5,6-tetrahydropyridine (1 mole; *Helv. Chim. Acta* 49 (1966) at p.694) 1 mole is added to a mixture of and sulfuric acid (4 moles) and stirred at 0° C. in an autoclave. The resulting mixture is stirred and heated to 65° C. for 45 minutes, cooled to 25° C., and then added slowly to twice its weight of water maintained at 5°–25° C. with cooling. The resulting aqueous mixture is stirred and neutralized to pH 8 by addition of 25 wt % aqueous NaOH and is then extracted with diethyl ether. The diethyl ether extracts are evaporated to a residue of non-volatile reaction products, from which the HALS product is isolated by recrystallization, distillation, or HPLC.

EXAMPLE 21

Preparation of THPB by condensation trimerization of 4-HAP

A 250 mL round bottom flask equipped with a magnetic stirrer, a Dean-Stark trap and a condenser is charged with 4-HAP (0.05 m), aniline (0.2 moles), and toluene (100 ml). The reaction mixture is heated at reflux under nitrogen atmosphere for 17 hours. Aniline hydrochloride (0.0038 moles) is then added, and toluene is removed via distillation. After being heated at 190°–200° C. for 3 hours, the reaction mixture is cooled to 120° C. Toluene (100 ml) is added to the cooled reaction mixture to separate an oil. After the supernate liquid is decanted, hexanes (100 ml) are added to the oily residue to precipitate 1,3,5-tris(4'-hydroxyphenyl)-benzene (THPB), which is recovered by filtration and which can be purified by recrystallization or HPLC. (yield: 79%).

Part of 4-HAP may be replaced by a different phenolic compound, to produce a substituted THPB as with THPE in the above examples. Also, the trimerization reaction in this example uses aniline as the condensation reagent. Instead, an acid catalyzed trimerization using, for example, HCl and triethyl orthoformate, may be employed.

Example 22

Following the procedure of example 7 generally, aromatic thiol is substituted in appropriate amounts to produce functionalized units including the structural unit:

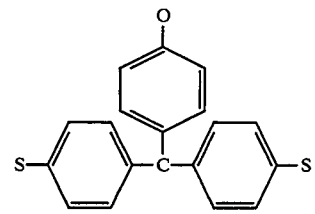

The inventive compounds prepared in accordance with examples above are particularly useful as stabilizers, flame retardants, colorants and the like when incorporated directly into a condensation polymer chain as described further hereinafter.

Examples 23–27

Preparation of Polysulfones Containing THPE-BZT

Polysulfones are typically prepared from equimolar amounts of dihydric phenols and 4,4'-dichlorodiphenyl sulfone as described in the *Encyclopedia of Polymer Science and Engineering*, Vol. 13, p. 196–211 (Wiley, 2nd. Editon, 1988). THPE-BZT prepared in accordance with the examples above was substituted for a portion of the stoichiometric amount of dihydric phenol, preferably in an amount of from about 0.05 to about 5 mole percent of the reaction mixture to produce the novel polysulfone polymers of the present invention as follows:

| Moles 4,4'-dichlorodiphenylsulfone | Moles Bisphenol A | Moles THPE-BZT |
|---|---|---|
| 1 | 0.90 | 0.1 |
| 1 | 0.95 | 0.05 |
| 1 | 0.99 | .01 |
| 1 | 0.995 | .005 |
| 1 | 0.999 | 0.001 |

Polymerization of the foregoing mixtures is carried out by way of the in-situ preparation of sodium or potassium salts of the dihydric phenol and reaction with the dichlorosulfone.

EXAMPLE 28

Polysulfone may be prepared as specifically described in this example

To a 3 neck 1-liter flask fitted with a thermowell, mechanical stirrer, and distillation head was added bisphenol(22.45 g, 0.098 mol), 4-fluorophenylsulfone (25.04 g, 0.098 mole) and potassium carbonate (27.09 g, 0.196 mol). Once all the reactants were added, 400 g of N-methylpyrrolidone and 50 g of toluene were added, and the mixture was stirred at room temperature until most of the reactants dissolved. The pale yellow solution was stirred while the temperature was raised from 25° C. to 65° C. over a two hour ramp. Removal of water was accomplished by azeotroping with toluene. The temperature was held at 165° for 16 hours, then ramped to 75° C. in five minutes and held there for 2 hours. The dark brown solution was allowed to cool to room temperature. The solution was decanted from the residual salts and precipitated into isopropanol/acidified water, 75/25. The resulting solid was filtered, redissolved into THF and precipitated again into isopropanol. The resulting white polymer was filtered and dried in a vacuum oven at 100° C. The intrinsic viscosity (IV) measured in tetrachloroethane at 30° C. was 0.35.

EXAMPLES 29-33

Further examples of THPE-BZT containing polysulfones are described in this section (THPE-BZT) (0.4155 g, 0.98 mol% based on bpA), bisphenol-A (22.37 G, 0.098 mol), 4-fluorophenylsulfone (25.24 g, 0.099 mol) and potassium carbonate (27.32 g, 0.098 mol) were added to a 3 neck 1-liter flask fitted with a thermowell, mechanical stirrer and distillation head. N-methyl pyrrolidone (400 g) and toluene (50 g) were added. The polymerization procedure described above was used. The resulting dark brown solution was precipitated into water containing ~1% HCl to neutralize any salts. The white flocculent polymer was filtered, extracted with methanol to remove any unreacted THPE-BZT and dried in a vacuum oven at 100° C. The white polymer had an IV of 0.29. UV analysis showed an absorption at $\lambda=335$ nm. The resulting polymer was then cast into a film and exposed to UV light. Yellowness index (YI) measurements were made hourly with a Hunter colorimeter on a series of polymers prepared in accordance with the above. Results appear in FIG. 1 and are compared with pure polysulfone and polysulfone containing commercially available additive (absorber A) that is blended with polymer.

EXAMPLES 34-36

Polycarbonates containing THPE-BZT substituted for a portion of the bisphenol-A were prepared by way of reaction with phosgene. This may be accomplished by any known method, however it was found preferable to carefully control the amount of excess phosgene present and pH as follows:

Suitable amounts of Bisphenol A, THPE-BZT are ground and added to a reactor with ammonium salt as well as $CO_3$ and $HCO_3$ buffer. The mixture is stirred. Methylene chloride is added and phosgene bubbled through while the pH is maintained at 9 through the addition of NaOH. Phosgene addition is continued only when the pH is approximately 9.

Results for a series of copolymers prepared in accordance with the above appear in FIG. 2 with levels of 0.5%, 1% and 2% mole per cent THPE-BZT.

EXAMPLE 37

Polyesters may be prepared by using THPE-BZT as a portion of the diol by condensation with a suitable dicarboxylic acid or a dicarboxylic acid derivative, for example acid chloride or diphenyl ester.

EXAMPLE 38

Preparation of Polyurethanes Containing THPE-BZT

Polyurethanes are prepared incorporating THPE-BZT by substitution of THPE-BZT for other polyols present in a reaction mixture. Examples are described in the *Encyclopedia of Polymer Science and Engineering*, Vol. 13, p. 243-303 (2nd. Edition, 1988, Wiley). As used herein, the term polyurethane refers to materials that include the carbamate function as well as other functional groups such as ester, ether, amide and urea. Polyurethanes are usually produced by the reaction of a polyfunctional isocyanate with a polyol or other hydroxyl-containing reactant. Since the functionality of the hydroxyl-containing reactant or the isocyanate can be adjusted, a wide variety of branched or cross-linked polymers can be formed. The hydroxyl-containing component may be of a wide variety of molecular weights and types including polyester and polyether polyols. The polyfunctional isocyanates may be aromatic, aliphatic, cycloaliphatic or polycyclic in structure and can be used directly as produced or modified. The flexibility in reactants leads to the wide range of physical properties of available materials. Present invention polymers are prepared by substituting THPE-BZT (from Example 4 above) for a portion of the hydroxyl-containing reactant in a mole ratio of THPE-BZT/hydroxyl from about 0.001:1 to about 0.1:1 for the polyol in a polyurethane reaction mixture or, in other words, from about 0.05 to about 5 mole percent of the total mixture as described above in connection with polysulfones.

EXAMPLE 39

Preparation of Epoxy Resins Containing THPE-BZT

Epoxy resins may be produced by reactions of epichlorohydrin and a hydroxyl monomer such as bisphenol A [2,2-di(4'-hydroxyphenyl)propane]. Examples are described in the *Encyclopedia of Polymer Science and Engineering*, Vol. 6., p. 322-382 (2nd. Edition, Wiley, 1988). When a portion of the hydroxyl monomer is replaced by THPE-BZT, such processes yield epoxy resins with covalently bound, non-migratory UV-light stabilizing functionality. The THPE-BZT may be added in any suitable amount, depending upon the reaction system selected, it being appreciated by those of skill in the art that perhaps the most important intermediate in epoxy resin technology is the liquid reaction product of excess epichlorohydrin and bisphenol A as noted above.

The invention has been described above in connection with numerous specific embodiments which are illustrative. Modifications and substitutions will be readily apparent to those of skill in the art, for example, the brominated compounds of the present invention may be substituted for THPE-BZT or diol when it is desired to impart flame—resistant properties to a polymer or the compound of Example 18 may be incorporated into a polymer as a stain blocker. Such modifications are within the spirit and scope of the present invention which is limited and defined only by the appended claims.

What is claimed:

1. A tris(hydroxyphenyl) ethane compound selected from the group consisting of:

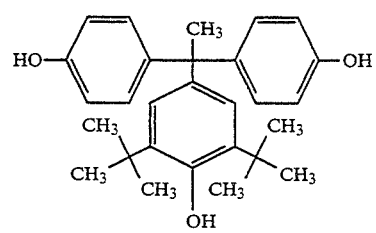

-continued
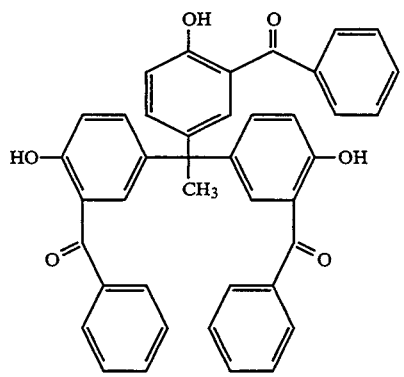
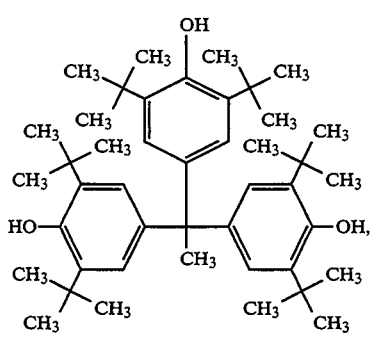
-continued
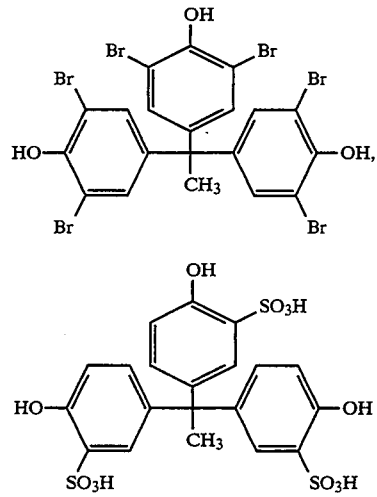
or
2. 1-(3'-(benzotriazol-2''-yl)-4'-hydroxyphenyl)-1,1-bis(4-hydroxyphenyl) ethane.
* * * * *

UNITED STATES PATENT AND TRADEMARK OFFICE
CERTIFICATE OF CORRECTION

PATENT NO. : 5,438,142
DATED : August 1, 1995
INVENTOR(S) : John R. Fritch et al It is certified that error appears in the above-indentified patent and that said Letters Patent is hereby corrected as shown below:

On the title page, item [75] and [19], correct the last name of the first inventor "Fritsch" to --Fritch--.

Signed and Sealed this

First Day of October, 1996

Attest:

BRUCE LEHMAN

Attesting Officer    Commissioner of Patents and Trademarks